United States Patent
Flint

(10) Patent No.: US 7,135,031 B2
(45) Date of Patent: Nov. 14, 2006

(54) REPEATED USE TROCAR-NEEDLE INSERTION INSTRUMENT AND LOADING TOOL

(75) Inventor: Michael Flint, Kiryat Tivon (IL)

(73) Assignee: Waismed Ltd., Tefen (IL)

( * ) Notice: Subject to any disclaimer, the term of this patent is extended or adjusted under 35 U.S.C. 154(b) by 61 days.

(21) Appl. No.: 10/891,852

(22) Filed: Jul. 15, 2004

(65) Prior Publication Data

US 2005/0033235 A1 Feb. 10, 2005

Related U.S. Application Data

(63) Continuation of application No. PCT/IL03/00082, filed on Feb. 2, 2003.

(30) Foreign Application Priority Data

Feb. 4, 2002 (IL) .................................... 147983

(51) Int. Cl.
*A61B 17/34* (2006.01)
*A61B 17/56* (2006.01)

(52) U.S. Cl. ..................... 606/185; 604/264; 606/53

(58) Field of Classification Search ............... None
See application file for complete search history.

(56) References Cited

U.S. PATENT DOCUMENTS

| 5,242,427 | A | * | 9/1993 | Bilweis ................. 604/264 |
| 5,368,046 | A | * | 11/1994 | Scarfone et al. ........... 600/567 |
| 5,591,188 | A | * | 1/1997 | Waisman ................. 606/182 |
| 6,066,146 | A | * | 5/2000 | Carroll et al. ............ 606/148 |
| 6,607,509 | B1 | * | 8/2003 | Bobroff et al. ............ 604/136 |

* cited by examiner

*Primary Examiner*—Glenn K. Dawson
(74) *Attorney, Agent, or Firm*—Frishauf, Holtz, Goodman & Chick, P.C.

(57) ABSTRACT

A single shot trocar-needle insertion instrument is configured for repeated use. The repeated use trocar-needle insertion gun (RUTI) operates in association with a loading tool, which for reloading, is coupled with the RUTI via a loading opening. The loading tool reloads the RUTI without requiring disassembly of the shooting mechanism. The loading opening is provided either ready open, or closed but openable in situ, where the insertion of the trocar-needle is administered. It is possible to implement a RUTI by entering a loading opening in an existing single shot trocar-needle insertion instrument (SSTI). After reloading the RUTI by help of the loading tool, a catch is operated, and, after mounting a trocar-needle and a front portion, the RUTI is returned to operative condition.

14 Claims, 8 Drawing Sheets

REPEATED USE TROCAR-NEEDLE INSERTION INSTRUMENT AND LOADING TOOL

This application is a Continuation of PCT/IL03/00082 filed Feb. 2, 2003.

TECHNICAL FIELD

The present disclosure relates to instruments for the insertion of a trocar-neelde into the marrow of a bone and more particularly, to apparatus and a system with a repeated use instrument and a loading tool configured for reloading the repeated use instrument for further use.

PRIOR ART

U.S. Pat. No. 5,591,188, to Waisman, referred to as the Waisman patent, which is incorporated herewith in whole by reference, discloses a surgical instrument, for impact insertion of an intraosseous trocar-needle. An improved version, named single shot trocar-needle insertion instrument, or SSTI, is produced by the Waismed Ltd., of Caesarea, Israel.

The SSTI is used to insert a trocar-needle into the bone marrow of a patient to permit connection of a syringe, an infusion set, or the like. The SSTI has a housing containing a sliding bolt biased by a spring for forcefully "shooting" a trocar-needle through a bone into the marrow, following release of the compressed helical spring. The bolt holds the trocar-needle in a releasable grip permitting the release of the needle, which remains in the bone. Prior to insertion, the helical spring is held in compressed state by a catch, which is releasable by pressure on a trigger. The spring, bolt, catch and trigger form the operative or shooting mechanism, designed to expel the bolt and the needle forwards. After release of the catch, the bolt is stopped and the needle, now inserted in the bone, is released from the instrument. Following penetration, the needle is connected to a syringe or an infusion set for intraosseous injection, and the spent SSTI is discarded.

For reasons of hygiene, medical instruments, which come into contact with a patient, are discarded to prevent potential contamination. Syringes and their needle are a know example, and the same holds for trocar-needle insertion instruments, or trocar-needle "guns". However, there are instances when it makes sense to reload a single shot trocar-needle insertion instrument, or SSTI. For example, in case of accident, when there is a lack of spare SSTIs, or a shortage thereof, and the same patient requires a repeated trocar-needle insertion, then it is often not only sound but imperative to utilize the same instrument again.

Another example for the need of a repeated use of instruments relates to the training of personnel. To become proficient, a user of the instrument needs to administer many insertions in the course of the instruction period, to become familiar with different conditions since these change with the location of the insertion as well as with the kind of patients such as babies, children, adults and elderlies, to name only a few. To save on training expenses, an instrument reconfigured for repeated use in mock insertions is certainly an acceptable proposition.

There is thus a need to provide instrument and a tool, or apparatus, and a system with a trocar-needle insertion instrument configured for repeated use.

There is a further need to provide apparatus and a system for the reloading of the trocar-needle insertion instrument, for use with the same or with a new trocar-needle.

Still another need is to provide a loading tool for reloading of the trocar-needle insertion instrument, for further use without requiring disassembly of the operative mechanism.

Yet another need is to design the loading tool for operation in-situ, where the insertion was applied to a patient

DISCLOSURE OF THE INVENTION

There is disclosed apparatus, i.e. a repeated use trocar-needle insertion instrument and a loading tool, and a system with a repeated use trocar-needle insertion instrument associated with a loading tool for reloading the insertion instrument, thereby providing repeated use.

The repeated use trocar-needle insertion instrument, or RUTI, handles and operates like an SSTI by release of a loaded spring to shoot a needle into the marrow of a bone. However, the RUTI is configured to match a loading tool necessary to reload the released spring of a spent RUTI.

The loading tool is mated with the RUTI to reload the spring, after which a catch is engaged to retain the spring compressed. Once reloaded, the loading tool is retrieved and a trocar-needle, previously used or new, is attached to the RUTI for repeated operation.

SUMMARY

In response to the need for a RUTI (repeated use trocar-needle insertion instrument), an instrument and a loading tool, or a system comprising an instrument for repeated use when reloaded by a loading tool is provided. For the sake of economy, the RUTI is achieved by modifying an existing product. The method used for implementation results in simple apparatus and system configured for loading a RUTI in situ, where the instrument is used.

It is an object to provide a RUTI comprising an operative mechanism and at least one loading opening configured for loading the RUTI for repeated use, thereby obviating disassembly of the operative mechanism to permit repeated use. The at least one loading opening may consist of one single loading opening, such as a one single bore.

It is an object of the present invention to provide a RUTI operating in association with a loading tool, comprising at the RUTI:

a needle portion configured for gripping a trocar-needle before insertion into a bone, and for release of the trocar-needle upon insertion into the bone, a front portion for adjusting insertion depth of the trocar-needle and for protecting the trocar-needle prior to release, and a rear portion comprising an operative mechanism for shooting the trocar-needle, and a catch for releasably retaining the operative mechanism until triggered for shooting, and further comprising:

a housing defining an inside, an outside and a bottom, at least one spring located inside the housing and residing in a first compressed condition associated with a loaded state of the RUTI before release of the operative mechanism, and in a second released condition associated with a spent state of the RUTI after release of the catch, the RUTI being characterized in that:

the bottom of the housing accommodates at least one loading opening to provide access therethrough, from the outside to the inside, for coupling with the at least one spring, and for coupling with the loading tool, whereby the RUTI and the loading tool are operatively associated to reload the RUTI in situ from the spent state to the loaded state via the at least one loading opening.

The at least one loading opening in the RUTI obviates the need for disassembly of the rear portion of the RUTI, when using the loading tool to reload the RUTI from the spent state to the loaded state. Moreover, the at least one loading opening in the RUTI may comprises one single bore, via which the loading tool is operable to reload the RUTI.

It is another object of the present invention to implement a RUTI by accommodating an SSTI with at least one loading opening in the SSTI bottom, whereby a RUTI is achieved by entering one single modification to the SSTI.

The at least one loading opening in the housing of the RUTI is configured either as a ready-made open loading opening, or as an openable closed loading opening configured for intentional opening in situ. The at least one open loading opening indicates that the RUTI is configured for more than one single use. After being opened, the at least one intentionally openable closed loading opening is indicative of at least one prior use of the RUTI.

Once reloaded from the spent state to the loaded state, the RUTI becomes operative for at least one repeated use after grippingly mounting a trocar-needle and after coupling the front portion to the rear portion. The reloaded RUTI is operative with either one of both a previously used trocar needle and a new unused needle.

The at least one spring in the RUTI has a proximal end closer to the front portion, in alignment with a distal end farther away from the front portion. Furthermore, the loading tool provides at least one compression force application element entering from the outside to the inside of the housing of the RUTI via the at least one loading opening. Moreover, the at least one compression force application element applies compressive force to, and in alignment with, the proximal end and the distal end of the at least one spring, for return from the released condition to the compressed condition.

When the loading tool returns the at least one spring to the compressed condition, the catch of the RUTI is operable to releasably retain the operative mechanism.

The loading tool has a front tool portion and a back tool portion, the front tool portion being configured for operation in coupling support with the proximal end of the at least one spring. The back tool portion has an element configured for penetration from the outside to the inside of the RUTI via the at least one loading opening in support of the distal end of the at least one spring. Furthermore, the loading tool is configured for application of compressive force to the front tool portion and to the back tool portion, for return of the spring to the compressed condition.

The loading tool has a loading mechanism applying mutually compressive force and relative motion between both the distal and the proximal support, for return of the at least one spring to the compressed condition, while permitting operation of the catch to releasably retain the spring in the compressed condition.

In addition, the loading tool has a distal portion and a proximal portion fixedly aligned on the loading tool, and also aligned with the distal end and with the proximal end of the at least one spring of the RUTI. The proximal portion supports the proximal end and the distal proximal portion penetrates via the loading opening in support of the distal end, for the loading tool to force translation of one or both of the distal portion and the proximal portion, to compress the spring.

If desired, the loading tool is equipped with at least one actuator. The actuator operates the loading tool and allows locking of the catch when the compressed condition of the at least one spring is reached. The at least one actuator is at least a single one or a combination of actuators selected out of manual, pneumatic, hydraulic, electric and magnetic actuators. The one or more actuators may comprise a mechanism operating with the loading tool for automatic operation of the catch when the compressed condition is reached.

It is one more object of the present invention to provide a system with a RUTI and a loading tool. The RUTI comprises:

a needle portion configured for gripping a trocar-needle before insertion into a bone, and for release of the trocar-needle upon insertion into the bone, a front portion for adjusting insertion depth of the trocar-needle and for protecting the trocar-needle prior to release, and a rear portion comprising an operative mechanism for shooting the trocar-needle, and a catch for releasably retaining the operative mechanism until triggered for shooting. The RUTI further comprises:

a housing defining an inside, an outside and a bottom, at least one resilient biasing element located inside the housing and residing in a first compressed condition associated with a loaded state of the RUTI before release of the operative mechanism, and in a second released condition associated with a spent state of the RUTI after release of the catch.

The RUTI is characterized in that:

the bottom of the housing accommodates at least one loading opening to provide access therethrough, from the outside to the inside, for coupling with the at least one spring, and for coupling with the loading tool, whereby the RUTI and the loading tool are operatively associated to reload the RUTI in situ from the spent state to the loaded state via the at least one loading opening.

BRIEF DESCRIPTION OF THE DRAWINGS

In order to understand the invention and to see how it may be carried out in practice, preferred embodiments will now be described, by way of non-limiting examples only, with reference to the accompanying drawings, in which.

DETAILED DESCRIPTION

The principle of operation of a prior art SSTI (single-shot trocar-needle insertion instrument) is exposed below with reference to FIGS. 1 to 9. The SSTI is a "gun" that is supplied in a loaded state, able to "shoot" a trocar-needle assembly for forceful insertion into the marrow of a bone. After insertion and release of the needle, the SSTI is spent and is discarded.

Figure 1:
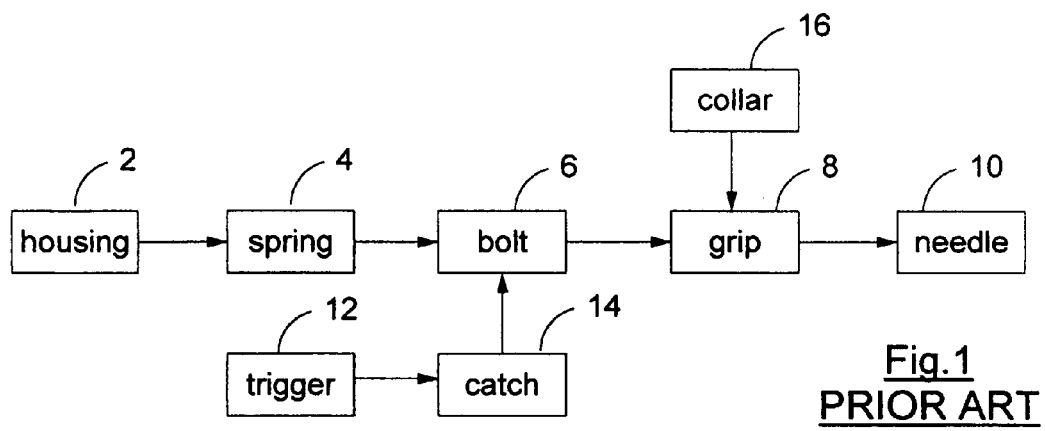
FIG. 1 is a block diagram illustrating the main components of an SSTI.

FIG. 1 symbolizes the main components of an SSTI represented as a housing 2, containing resilient biasing means 4, referred to below as the spring 4, and a bolt 6. The bolt 6 is a sliding assembly ending in a grip 8, which is an openable needle-gripping assembly holding the trocar-needle assembly 10, referred to below as the needle 10. To eject, or "shoot" the needle 10, the SSTI is applied to a patient, opposite a bone, not shown in FIG. 1, and a trigger 12 releases a catch 14, or bolt catch 14, that in turn, liberates the bolt 6. The spring 4 now expands to expel the bolt 6, and when almost fully extended, the grip 8 meets a collar 16 that releases the needle 10 from the grip, with the needle inserted in the bone. The same collar 16 also retains the spring 4 inside the housing 2. The SSTI is now spent, and purposely discarded.

FIG. 1 is but schematic and does not refer to all the components of the SSTI. In the following description the terms "front", designated as F, "forward", or proximal, will be used to define the side closer to the bone and the direction of driving the needle into the bone, while the expressions "rear" indicated as R, "rearwards", "end", "bottom" or distal, will define the opposite direction and side, pointing away from the bone. Moreover, similar reference numerals refer to similar elements throughout all the Figures.

Figure 2:
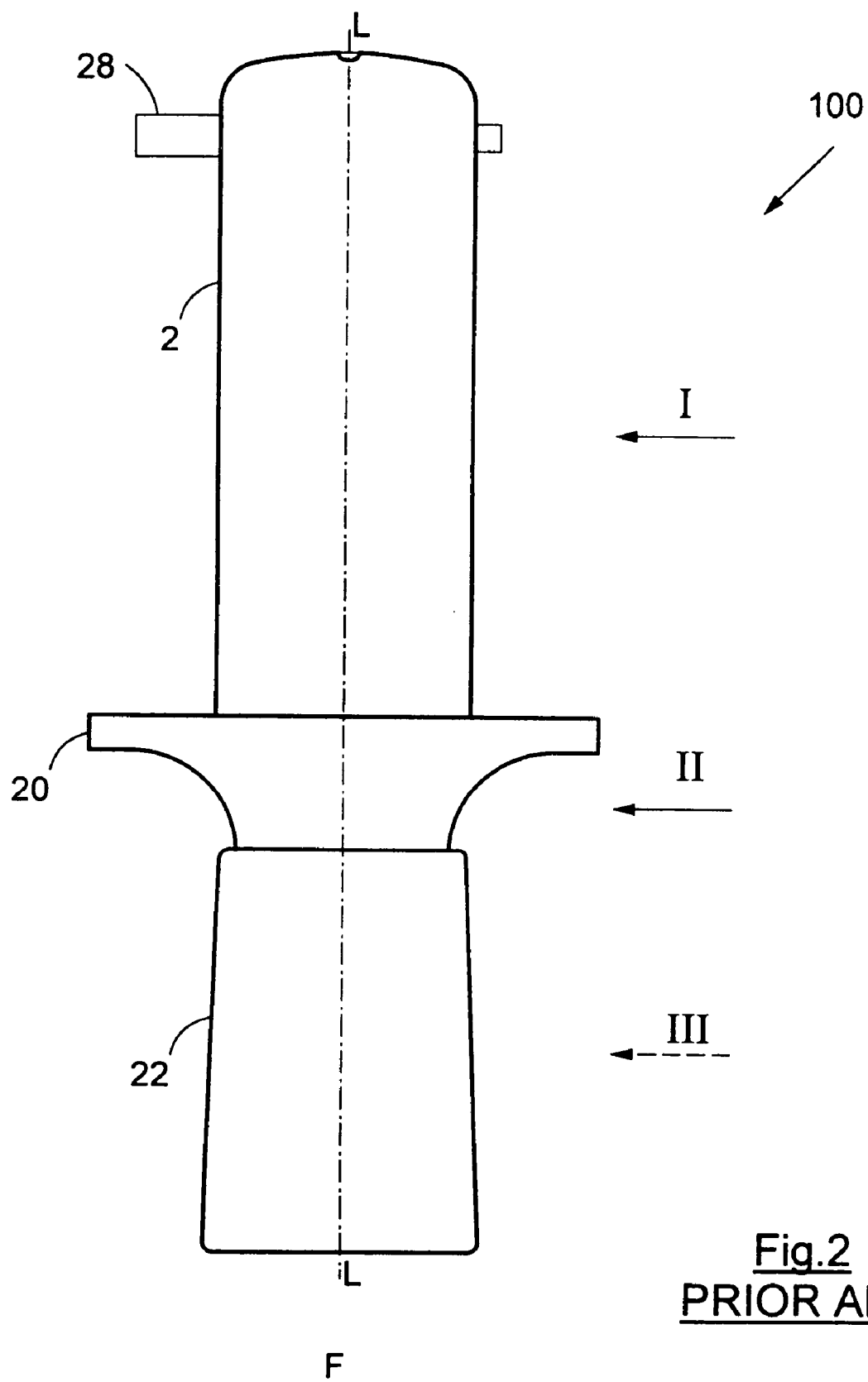
FIG. 2 is a plan view of an SSTI prior to operation.
Figure 3:
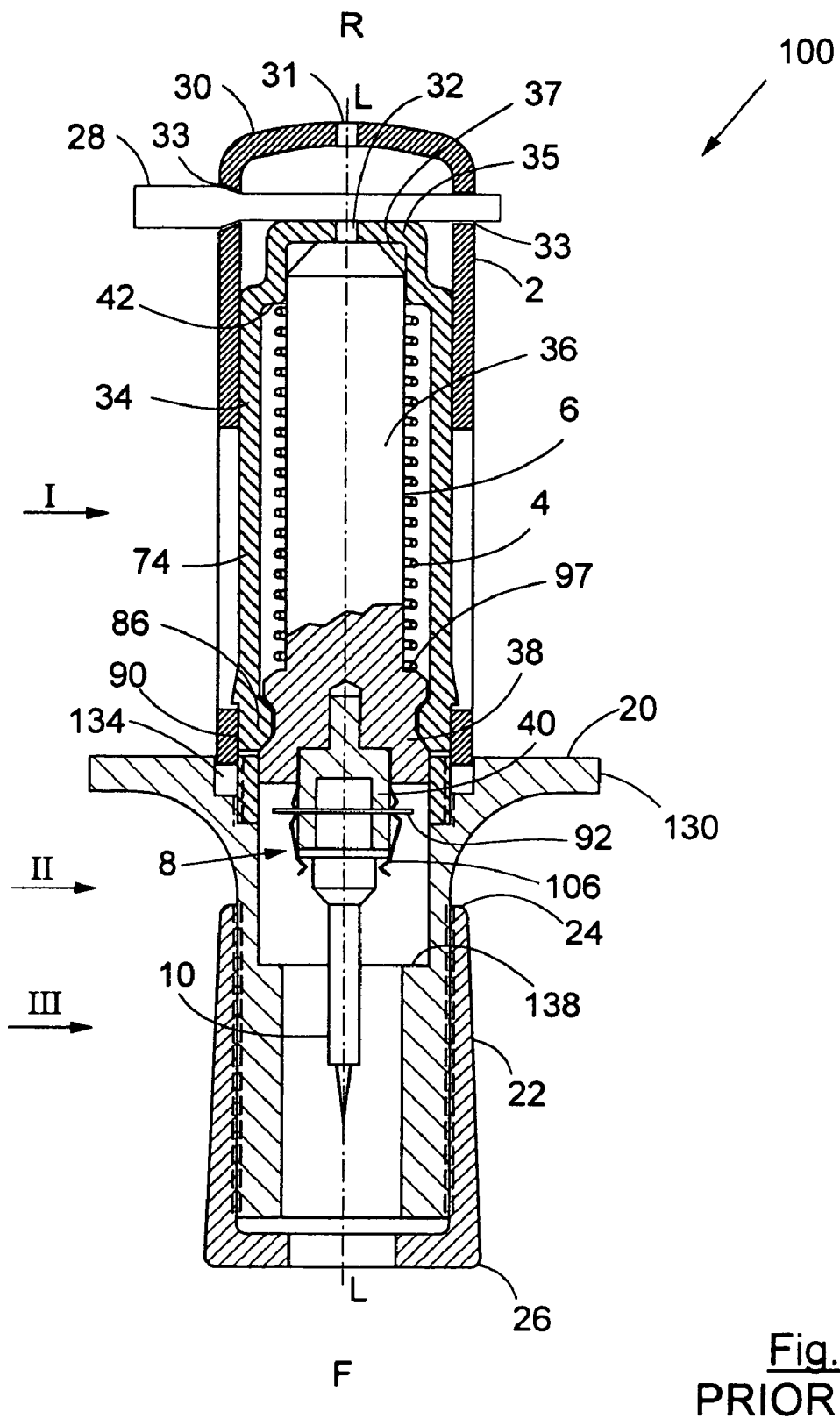
FIG. 3 is a longitudinal cross-section of the SSTI shown in FIG. 2.

FIGS. 2 and 3 show an embodiment 100 of the SSTI in the loaded state, ready for operation, as an assembly extending along a longitudinal axis L—L. The SSTI comprises a rear portion I, a front portion II, and a needle portion III hidden from view in FIG. 2 by the front portion II. The rear portion I comprises a housing 2 containing the operative or "shooting" mechanism. The front portion II features a gage 22 and a casing 20 protectively covering the needle 10 and hiding it from view. Most of the length of the casing 20 is concealed by the gage 22, permitting to adjust the depth of insertion of the needle. The gage 22 is located at the front of the SSTI and has a rear rim 24 and a front rim 26. A transversally rear-mounted safety 28, which is removably inserted transversally in the housing 2 to prevent accidental operation of the SSTI 100, is the only component not in alignment with the longitudinal axis L—L common to all the other components of the SSTI.

Externally, the discernable difference between a loaded and a spent SSTI 100 is indicated by the released state of the spring 4 and by the missing safety 28. The housing 2, being made of transparent material, permits to visually distinguish between the compressed and the released state of the spring 4. More obvious is the presence or the absence of the safety 28.

FIG. 3 is a longitudinal cross-section of the loaded and safety-secured SSTI 100, revealing all the components.

The housing 2 is substantially a hollow cylindrical body with a bottom 30, closed and integrally formed in a dome-like shape with the convex side pointing rearward, and may have a concentric small diameter housing perforation 31 in the bottom. Adjacent thereto, two diametrically opposed passages 33 permit protruding transversal insertion of the safety 28, extending out of the housing 2, on both opposite sides.

A jacket 34, configured as a cylindrical transparent tube, is received concentrically inside the housing 2. The rear end 35 of the jacket 34 has a reduced diameter and is closed but contains an air passage small diameter jacket perforation 32, concentric with the housing perforation 31. The rear end 35 rests against the safety 28.

The spring 4, depicted as a coil spring in FIG. 3, is slidingly guided by the inside walls of the jacket 34. A shank 36, being the rear portion of the bolt 6, is supported by a reduced diameter rear concentric support 37 at the rear end of the jacket 35. The spring 4 is internally slidingly guided on the shank 36.

At the front, the bolt 6 further comprises a piston 38 fixedly seizing a head 40 that securely holds the grip 8. The outer diameter of the piston 38 is larger than the diameter of the shank 36, which allows retention of the spring 4 in a compressed condition between the rear of the piston 38 and between a rest 42, resulting from the inner diameter reduction forming the concentric support 37, inside the rear of the jacket 34.

A needle 10 is releasably coupled to the grip 8, in alignment with the axis L—L. In concentric alignment, the casing 20 is attached by a screw thread to the front of the jacket 34 and covers the whole length of the needle 10. The gage 22, with a rear rim 24 and a front rim 26, is in screw-threaded engagement over the casing 20, and permits to regulate the depth of penetration of the needle 10 inside the bone. The more unscrewed forwards, the less will the needle 10 penetrate the bone. Markings, not shown in FIG. 3, entered on the exterior of the casing 20, provide an indication of the depth of penetration of the needle 10 into the bone.

The housing 2, the jacket 34 and the bolt 6 operate as a catch and mutually cooperate to ascertain the retention of the spring 4 in the compressed condition and to permit triggered discharge thereof to the released condition.

Figure 4:
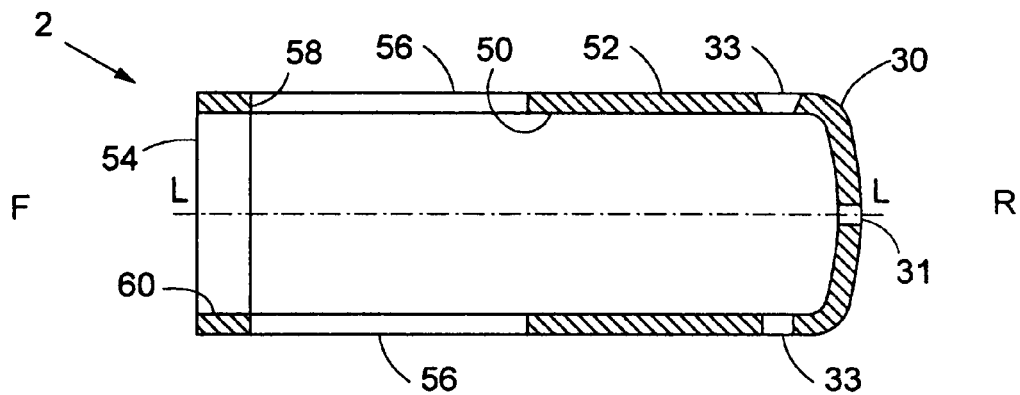
FIG. 4 is a longitudinal cross-section of the housing shown in FIG. 2.

With reference to FIG. 4, the housing 2 is shown as a hollow cylinder with smooth surfaces at the inside 50 and the outside 52, from the bottom 30 at the rear end, to the front opening 54. Two longitudinal windows 56 are opened on diametrically opposite sides of the housing 2, in alignment with the longitudinal axis L—L and if so desired, with the passages 33. Each window 56 has a front wall 58 that defines an inner annular surface 60 delimited between the front wall 58 and the front opening 54. Explanations below describe how these elements cooperate with the jacket 34 and the bolt 6.

Figure 5A:
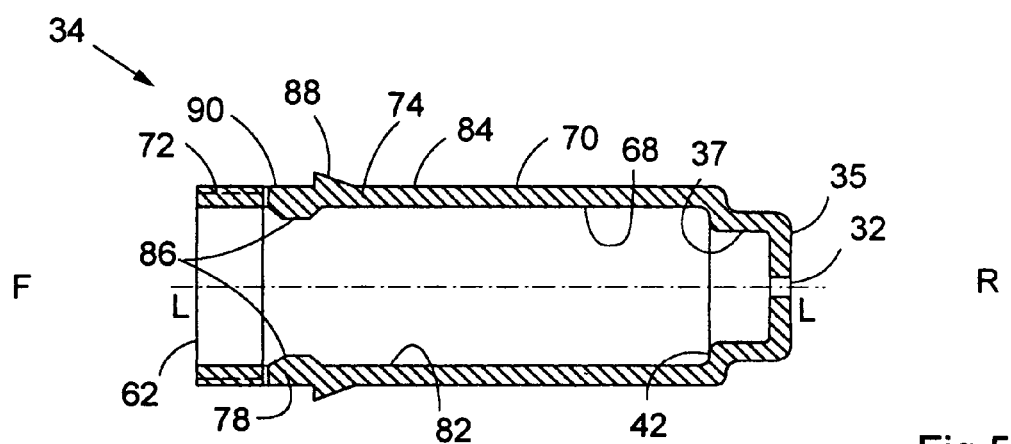
FIG. 5 depicts the jacket shown in FIG. 2, with a longitudinal cross-section 5a and a plan view 5b.
Figure 5B:
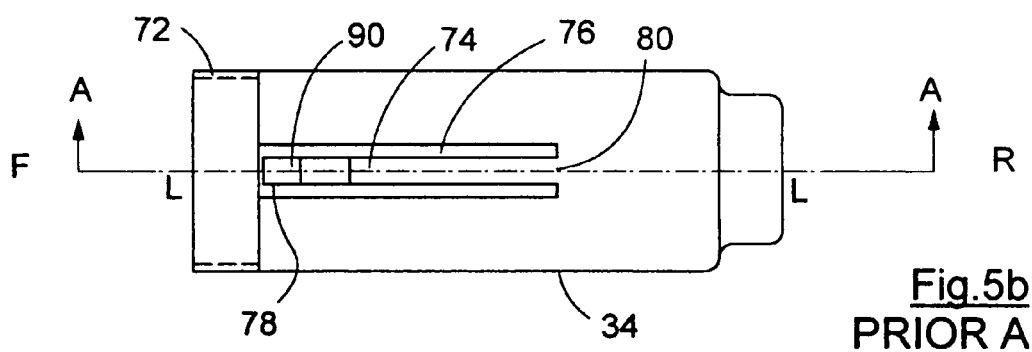

FIG. 5a is a section of FIG. 5b cut along the axis L—L, following the arrows A. In FIGS. 5a and 5b, the jacket 34 is shown as a substantially hollow cylinder comprising a front opening 62, and at the rear, a rear end 35 with a jacket perforation 32 of about the same diameter as the housing perforation 31, and a smooth inner and outer surface, respectively 68 and 70. The reduced diameter at the rear-end 35 of the jacket 34, forms the rest 42 and the concentric support 37. Adjacent the front of the jacket 34, and on the outer surface 70, there is a provided an external screw thread 72.

Two tongues 74 are cut out in longitudinal alignment on diametrically opposite sides of the jacket 34 to form two flexible resilient cantilever beams. A narrow slit 76 surrounds the tongues 74 on three sides, which have a free end 78 and an attached end 80. The width of each tongue 74 is predetermined to permit deflecting penetration within a corresponding window 56 of the housing 2. When an appropriate loading force is applied perpendicularly to the free end 78 of a tongue 74, a sinking deflection towards the axis L—L is achieved for a radially inward load, and for a radially outward load, a protruding deflection extending outwardly of the outer surface 70 is obtained.

Without loading forces being applied, most of the outer surface 84 of the tongue 74 is coextensive with the outer surface 70 of the jacket 34. In the same manner, without load, most of the inner surface 82 of the tongue 74 is also coextensive with the inner surface 68 of the jacket 34.

Adjacent the free end 78 and on the inner surface 82 of the tongue 74, a tooth 86 of trapezoidal cross section protrudes on the inner surface of the tongue, radially toward the axis L—L. Similarly, adjacent the free end 78 but on the outer surface 84 of the tongue 74, a shoulder 88 with a front wall raised radially outward of the surface of the tongue, is offset to the rear by the width of the tooth 86, leaving a support surface 90 forwards of the shoulder.

The concentric support 37 at the rear end of the jacket 35 provides sliding support to the rear end of the shank 36. It is noted that the outer diameter of the outer surface 70 of the jacket 34 is received in sliding fit by the housing inside 50.

Figure 6:
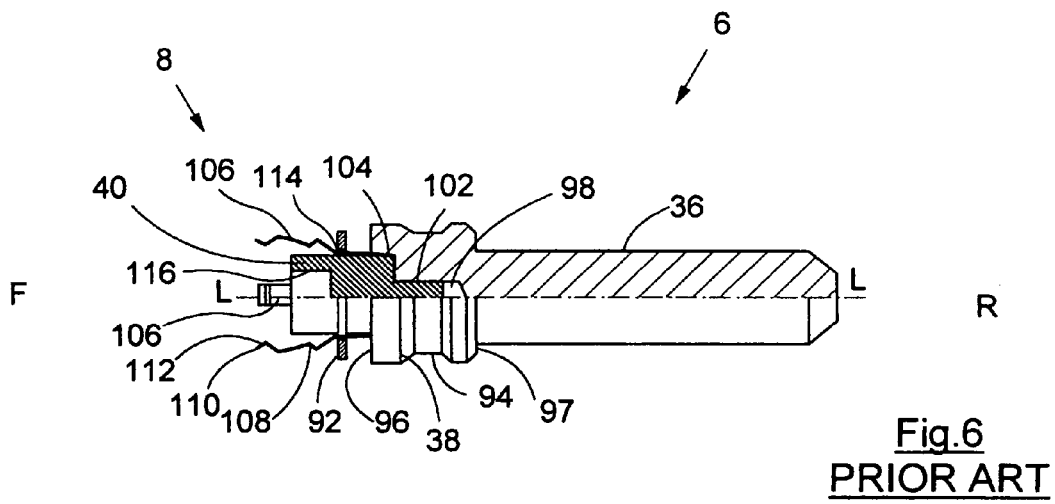
FIG. 6 illustrates in detail the bolt and the grip shown in FIG. 2.

FIG. 6 illustrates a longitudinal assembly of the bolt 6 with the grip 8 and the head 40. The head 40 fixedly retains the grip 8 comprising the washer 92. On the bolt 6, the piston 38 comprises a circumferential groove 94, on the outer diameter, featuring a trapezoidal cross-section, configured to mate with the shape of the tooth 86 protruding on the inner surface 82 of the tongue 74. On the front vertical surface 96 of the piston 38, a concentric recessed bore 98 with a leading bore 102, a trailer bore 104 accommodates the head 40, which rigidly fixes the grip 8 to the piston 38 by pressure fit.

The grip 8, axially aligned with the bolt 6, features, for example, four independent fingers 106, naturally open, extending radially outwards and forwardly of the bolt 6. It is noted that the front finger 106 is deleted form FIG. 6 to allow a better view. Each finger 106 forms a cantilevered spring configured with a notch 108, intermediate the front surface 96 and the free end 110 of each finger, and with an outward slant 112 formed at the free end 110 of the finger. The washer 92 freely straddles the fingers 106 when adjacent the front surface 96 of the piston 38. By forceful forward displacement of the washer 92 until seated inside the notch 108, the fingers 106 are urged radially inwards towards each other by the washer bore 114. When closed by the washer 92, the grip fingers 106 receive and firmly retain the needle assembly lo. Evidently, backing-up the washer 92 rearwards, thus towards the front surface 96 of the piston 38, will open the fingers 106 to release the needle assembly 10. It is noted that the front of the head 40 comprises an alignment bore 116 configured to receive the needle 10.

Figure 7:
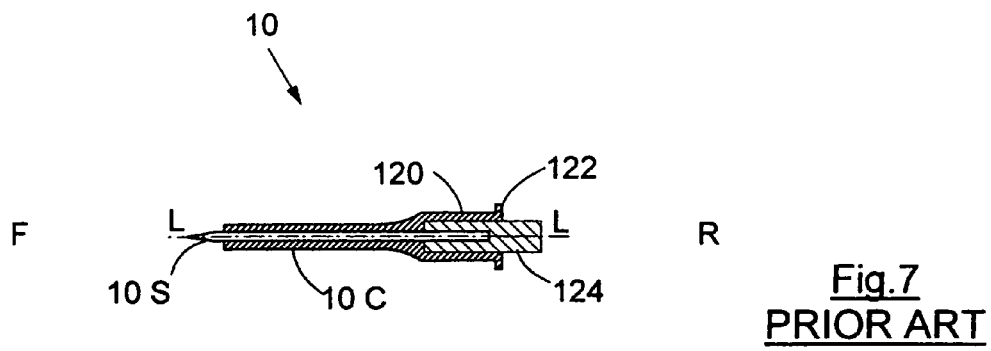
FIG. 7 shows a cross-section of a trocar-needle assembly, as seen in FIG. 2.

In FIG. 7, the needle 10 is shown as an assembly according to the description found in the Waisman patent. The needle assembly 10 comprises a stylet 10S enclosed in a cannula 10C which includes a hollow cylindrical base 120 at the rear end, terminating in a flange 122 forming a rim at the extreme outer end of the cylindrical base. The rear end of the stylet 10S which is firmly embedded in a block 124 of cylindrical shape, which shape is inserted into the hollow base 120 and concentrically protrudes outside therefrom. The block 124 mates with the alignment bore 116 in the head 40 and the connecting flange 122 is retained by the fingers 106 when the needle 10 is assembled with the grip 8. After insertion into a bone, the block 124 together with the stylet 10S are withdrawn.

Reference is now made again to FIGS. 3 to 8. When the SSTI is assembled, the spring 4 surrounds the shank 36 of the bolt 6, inside the jacket 34. Both teeth 86 of the tongues 74 engage the groove 94 of the piston 38, while the support surfaces 90 of the tongues 74 are retained by the inner annular surface 60 at the front of the housing 2. The compressed spring 4 is thus supported at the front end by the rear surface 97 of the piston 38 and at the rear end, by the rest 42. To prevent any unintended backward translation of the jacket 34 relative to the housing 2, the safety 28 is introduced into the passages 33.

The needle 10 is retained by the grip 8, or more precisely, the fingers 106 are closed on the hollow base 120 in front of the flange 122, by the washer 92, which is seated in the notch 108. The casing 20 is threadingly engaged with the jacket 34 and surrounds the needle 10.

Figure 8:
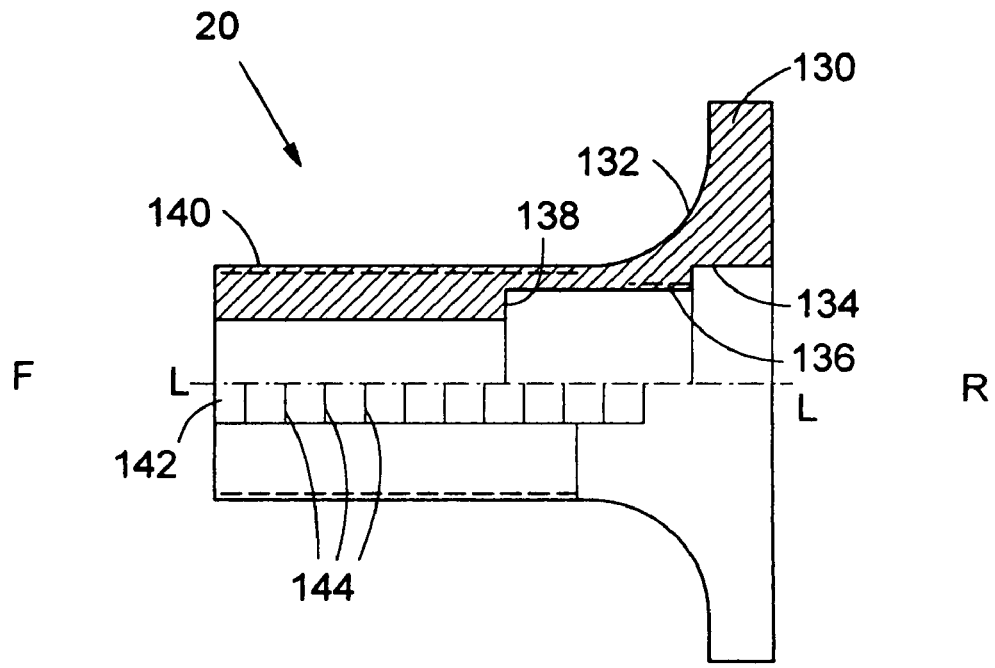
FIG. 8 depicts the casing shown in FIG. 2, in half cross-section.

With reference to FIG. 8, the casing 20 is an axially aligned hollow handle with two arms 130 extending radially outwards in diametrically opposite direction to the longitudinal axis L—L, having a front curve 132 accommodated to fit the fingers of a hand.

The rear end of the casing 20 features a cylindrical relief 134 of a diameter fit to receive the outer diameter of the housing 2, and with a depth sufficient to accept the width of the inner annular surface 60. Forwards of the relief 134, an inner screw thread 136 in the inside of the hollow casing 20 is provided for engagement with the external screw thread 72 of the jacket 34. Also inside the hollow casing 20, forwards of the inner thread 136, a diameter reduction forms a step 138. Finally, the front outer portion of the casing is covered with an external gage screw thread 140, for screw threaded engagement with the gage 22. A narrow longitudinal flat 142 depressed below the surface of the screw threads 140 carries annotated graduation marks 144, seen only partially in FIG. 8, that indicate the depth of penetration of the needle 10 in the bone, relative to the position of the rear rim 26 of the gage 22.

Figure 9:
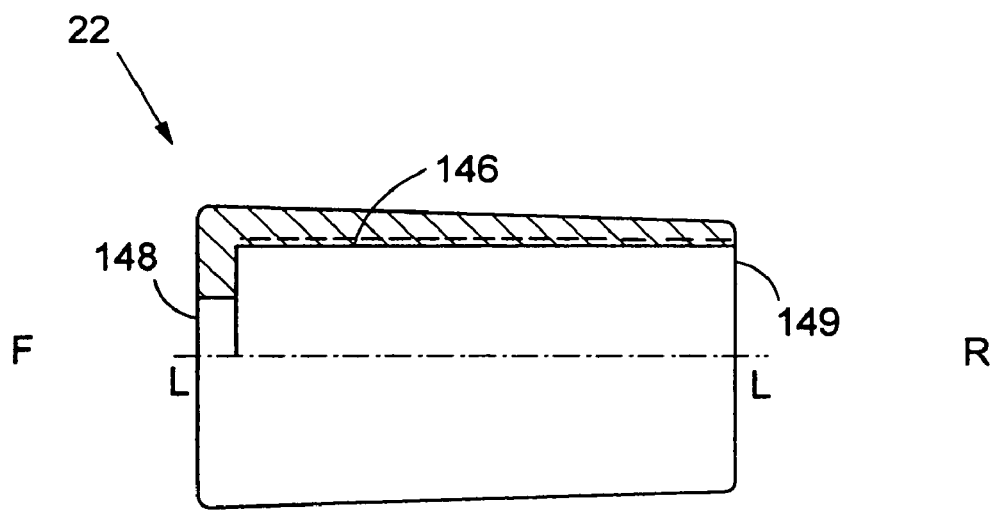
FIG. 9 shows the gage of FIG. 2, in half cross-section.

FIG. 9 depicts the gage 22, showing an inner screw thread portion 146, an exit opening 148 and an entry opening 149. As explained above, the gage 22 is retained by the inner screw thread portion 146, over the casing 20, which engages the external gage screw thread 140.

The SSTI is thus a gun or a tool having a needle portion configured for gripping a trocar-needle before insertion into a bone, and for release of the trocar-needle upon insertion into the bone. The SSTI has a front portion configured for adjusting the insertion-depth of the trocar-needle into the bone, and for protecting the trocar-needle prior to release. The SSTI also has a rear portion having a shooting mechanism operative for shooting the trocar-needle, and a catch adapted for retaining the shooting mechanism, and for releasing the shooting mechanism when triggered for shooting, with the front portion being releasably coupled to the rear portion.

The rear portion of the SSTI has a housing having a housing inside, a housing outside, and housing bottom. Furthermore, the rear portion has at least one spring disposed inside the housing and residing in a first compressed condition associated with a loaded state of the SSTI before shooting the trocar-needle, and with a second released condition associated with a spent state of the SSTI after shooting the trocar-needle.

Operation of the SSTI

The following description refers to a loaded SSTI 100, according to FIG. 3.

Before operation, the depth of insertion of the trocal needle 10 is adjusted by screw-threading the gage 22 over the casing 20 until the selected depth is reached, as read on the graduations 144. Then, the SSTI 100 is held with the convex bottom 30 pushing against the palm of the hand and with one finger pressing against each one of the front curves 132 of the arms 130, in the casing 20. The front end of the gage 22 is applied to the location for insertion of the trocar-needle 10 and the safety 28 is extracted from the passages 33. For actual insertion, by release of the operative mechanism, thus for triggering or shooting the trocar-needle 10, the front curves 132 are retracted by the two fingers towards the palm of the hand. The housing 2, not retained by the safety 28, translates over the jacket 34, and the inner annular surface 60 slides over the support surfaces 90 and enters into the relief 134 of the casing 20. When the support surface 90 separates from the annular surface 60, the tongues 74 are free to deflect radially outward. Then, under the load applied by the spring 4 on the piston 38, the teeth 86 are pushed out of the groove 94 and the tongues 74 lift radially outwards into their respective window 56. The piston 38, once freed, allows the bolt 6 to jump forwards under the force exerted by the spring 4 against the rest 42 in the jacket 34. The needle 10 is now projected forwards out of the casing 20 and out of the gage 22 via the exit opening 148. On the way out, the washer 92 impacts on the step 138 to be brutally arrested thereby, while the bolt 6 continues on its trajectory. Freed from the washer 92 that now abuts the front surface 96 of the piston 38, the fingers 106 open-up and release the needle 10. After release of the needle 10, the SSTI 100 is now in the spent state, as indicated by the released spring 4 and the missing safety 28.

Detailed Description of the Repeated Use Trocar-Neede Insertion Instrument (RUTI)

To reconfigure an SSTI into a RUTI thus as an instrument able to be reloaded, with reference to FIG. 1, the spring 4 is first recompressed, next the bolt 6 is re-engaged with the catch 14, and a needle 10 is reinstalled into the grip 8, It is noted that the terms "loading" and "reloading", thus "loading again", relate to the same loading operation and have the same meaning.

For reload, an SSTI has to be reconfigured into a RUTI to allow approach to the spring 4 and to permit handling of the components involved in the reloading operation. Further, nearness to the spring 4 is necessary but without requiring disassembly of the operative, or "shooting" mechanism of the reconfigured SSTI. Third, the reloading for repeated use must be operable in situ in the field, wherever the instrument is used, without restricting reloading to a laboratory, to a service facility, or to a plant. Fourth, an appropriate tool must be devised to facilitate the reloading of the spent instrument when the STTI is reconfigured into a RUTI.

The SSTI 100 currently on the market is purposely not configured for reloading from the spent state to the loaded state. To permit reloading for repeated operation, there is need for two devices, namely an insertion element and a loading tool, or for a system comprising both. However, since product development is expensive, advantage is taken from an existing product, such as an SSTI, to which sufficient but minimal modifications are applied. The resulting repeated use trocar-needle insertion instrument, or RUTI, is configured to mate with a loading tool enabling reloading for repeated use.

Figure 10:
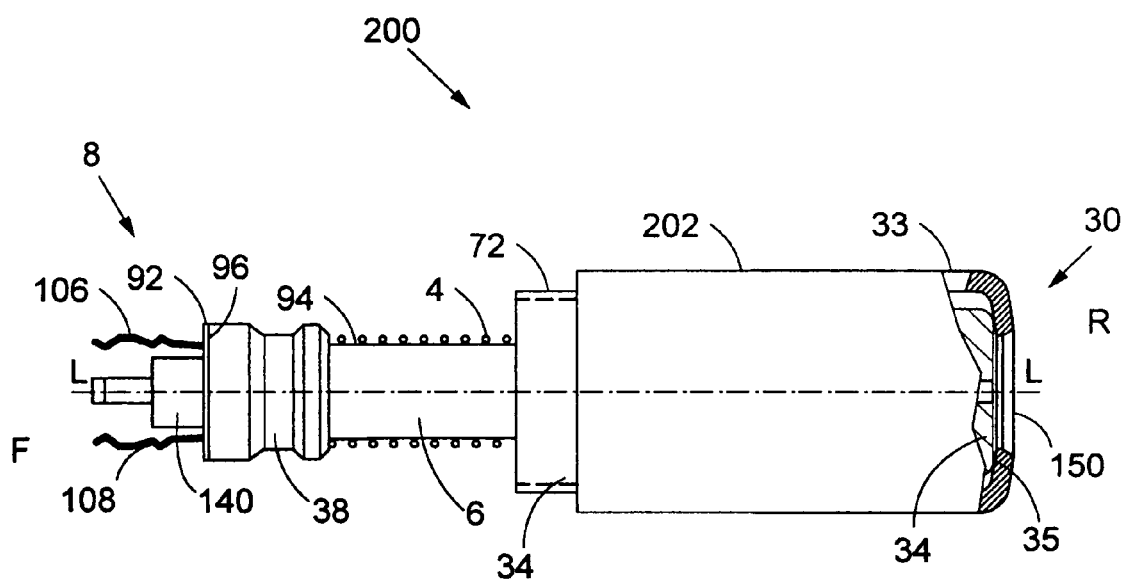
FIG. 10 illustrates a RUTI in the spent state.

FIG. 10 illustrates an embodiment 200 of a RUTI, hereafter RUTI 200, configured for repeated use. Although supplied with a compressed spring 4, thus in the loaded state, the RUTI 200 is shown in FIG. 10 after reaching the spent state and after removal of the casing 20 and the gage 22.

It is noted that the term "spring" is generic and relates to compression springs in general, and is not limited to coiled-metal springs, either single or multiple, but refers to resilient biasing means that comprises elastromeric as well as synthetic material springs. Although the description and examples refer to a coiled metal spring 4, the principles involved are similar for other spring configurations.

The spring 4 is seen to protrude forwards of the jacket 34, in the released condition. Accordingly, the bolt 6 is supported by the extended spring 4, with the piston 38 protruding frontwards and out of the jacket 34. The washer 92 abuts the front surface 96 of the piston 38, allowing the fingers 106 of the grip 8 to open widely apart, radially and outwardly. In the bottom 30 of the housing 202 of the RUTI 200, there is entered a loading bore 150, or open loading opening 150. The inner diameter of the open loading opening 150 is about half the exterior diameter of the housing 202. When compared, the SSTI 100 and the RUTI 200 are exactly the same, but for the open loading opening 150 accommodated in the housing 202 of the RUTI 200, which operates as an SSTI.

To reload a spent RUTI 200 after removal of the housing 20, which holds the gage 22, the first step is to shift the washer 92 away from the piston 38 and into the notch 108 of the fingers 106. Then, the spring 4 is returned to the compressed condition. To this end, access is made to the jacket back 35 via the loading opening 150. On the front side of the RUTI 200, the head 40 is firmly supported (not shown in FIG. 10) while the jacket 34 is forcefully pressed forwardly (not shown in FIG. 10), thereby compressing the spring 4. When the fully compressed condition of the spring 4 is reached, the catch is set by slidingly retracting the housing 202 backwards relative to the jacket 34, thereby allowing the inner annular surface 60 to cover the support surfaces 90 of the tongues 74, to lock the teeth 86 inside the groove 94 of the piston 34. The RUTI 200 is now in the loaded state. To prevent accidental release, the safety 28 (not shown in FIG. 10), is inserted to protrude through the passages 33.

The needle 10 is then inserted by pushing the block 124 onto the slants 112 at the free end 110 of the fingers 106. Pressure on the slants 112 opens the fingers 106 apart for insertion of the block 124 into the alignment bore 116 of the head 40. The fingers 106 now close over the flange 122 and grip the needle 10 by sliding the washer 92 into the notch 108. In turn, the casing 20, with the gage 22 engaged thereon, is threadingly screwed over the external screw thread 72 at the front of the jacket 34. The RUTI 200, now back in the operative state, is ready for repeated use. The large loading bore 150, and possibly a jacket back 35 featuring a bright vivid color, warn the user that the RUTI 200 is not a single shot device. The loading bore 150 thus conveys a tactile signal to the palm of the hand, and the colored jacket back 35 displays a visual indication, of the repeateduse nature of the RUTI 200. Although not shown in the FIGS., the RUTI 200, and another embodiment of a RUTI 300 described hereinbelow, carry a label indicating the ability to reload the instrument. In fact, a RUTI 200 is a SSTI 100 with an open loading opening 150, or with an openable loading opening.

It is noted that a safety 28 protruding out of the housing 202 proves that the RUTI 200 is loaded. Without the safety 28, a compressed spring 4, as seen via both the transparent housing 202 and the jacket 34, indicates that the RUTI 200 is loaded but not safely secured.

The RUTI is thus, if desired, a reconfigured SSTI for facile reloading, and operates in association with a loading tool.

Like the SSTI, the RUTI has a needle portion configured for gripping a trocar-needle before insertion into a bone, and for release of the trocar-needle upon insertion into the bone. The RUTI has a front portion configured for adjusting insertion-depth of the trocar-needle into the bone, and for protecting the trocar-needle prior to release out of the bone. The RUTI also has a rear portion having a shooting mechanism operative for shooting the trocar-needle, and a catch adapted for retaining the shooting mechanism, and for releasing the shooting mechanism when triggered for shooting, with the front portion being releasably coupled to the rear portion.

The rear portion of the RUTI has a housing having a housing inside, a housing outside, and housing bottom. Furthermore, the rear portion has at least one spring disposed inside the housing and residing in a first compressed condition associated with a loaded state of the RUTI before shooting the trocar-needle, and with a second released condition associated with a spent state of the RUTI after shooting the trocar-needle.

In addition, the RUTI has at least one open loading being accommodated in the bottom of the housing of the RUTI to provide access therethrough, from the outside to the inside, for coupling the loading tool with the at least one spring.

Finally, there is a loading tool configured for coupling with and operative for reloading the RUTI in situ from the spent state to the loaded state via the at least one loading opening.

If desired, a RUTI is derived out of an existing SSTI having an SSTI inside, an SSTI outside, and an SSTI bottom by entering at least one loading opening in the bottom of the SSTI, whereby a RUTI is implemented out of an SSTI by entering one single modification to the SSTI.

Loading Tool

Figure 11:
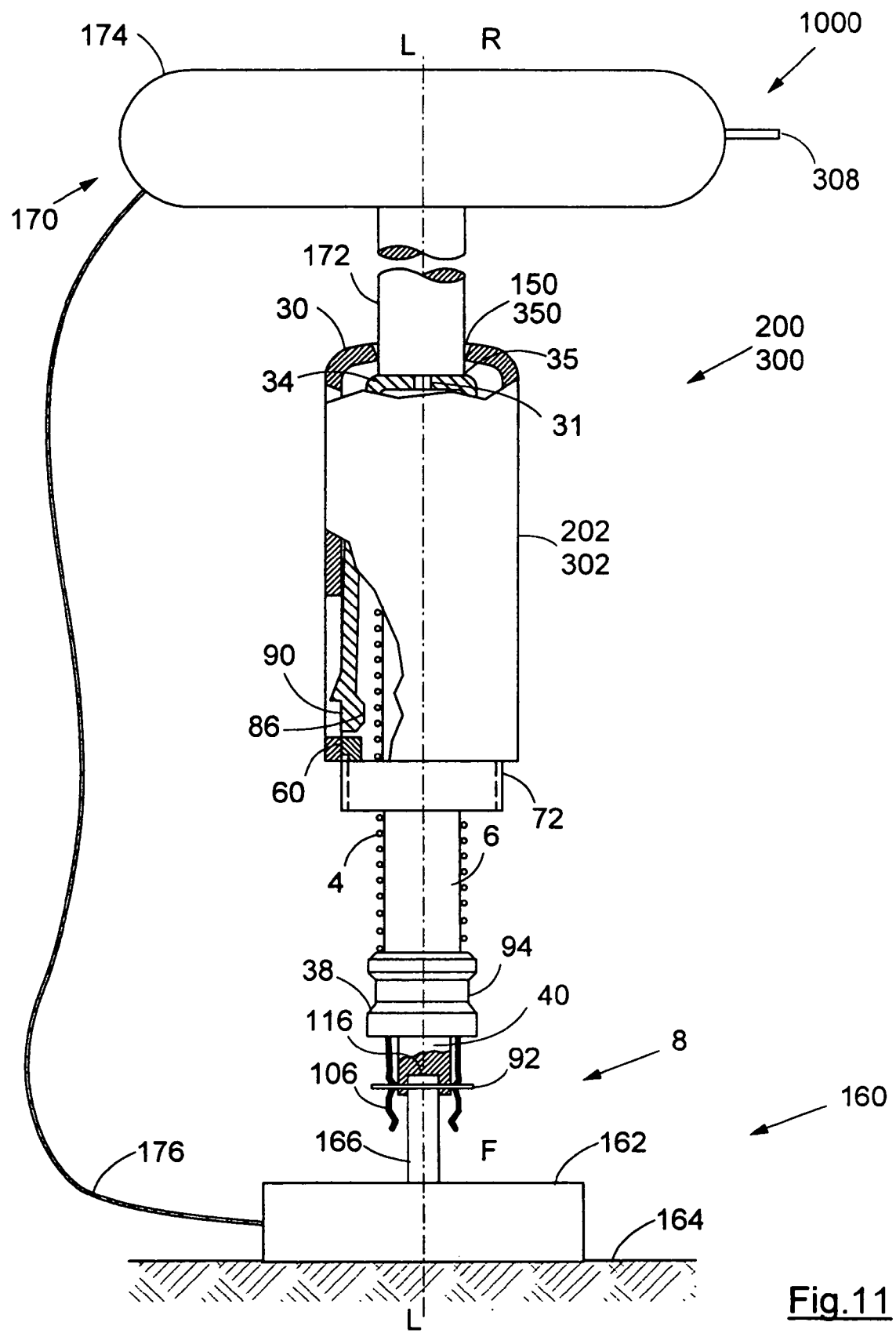
FIG. 11 depicts a first embodiment of a two-piece loading tool engaging a RUTI shown in FIG. 10, FIGS. 12a–c show further embodiments of the housing of the RUTI seen in FIG. 10.

In practice, the reloading operation of a RUTI is performed by help of a loading tool. Reference is now made to FIG. 11 showing an embodiment 1000 of a loading tool. The spent RUTI 200 is shown in vertical position with a front tool 160 and a back tool 170 designating respectively, a front tool portion and a back tool portion. The front tool 160 has a base 162 possibly resting, e.g. on a horizontal support surface 164, and a pin 166 fixedly connected to the base and perpendicular thereto. The back tool 170 carries a rod 172 fixedly retained and perpendicular to a handle 174 configured for ease of grasping by hand. The rod 172 features a diameter fitting for sliding passage into the loading opening 150, with a length sufficient to cover the travel of the spring 4 from the released condition to the compressed condition, while leaving ample room for the fingers of the hand between the handle 174 and the bottom 30 of the housing 202. The pin 166, the rod 172 and the RUTI 200 are thus all concentrically aligned with the longitudinal axis L—L. Evidently, reloading may be accomplished at any angle of attitude of the axis L—L convenient to the user and not only in the vertical position. As long as the loading tool 1000 and the RUTI 200 are mutually aligned, any angle for reloading is practical. Moreover, the loading tool 1000 is operable in-situ, in any location where the RUTI 200 is operated.

Since the loading tool 1000 has a base portion 160 and a handle portion 170, a thin cable 176, or string, may connect both portions, to prevent misplacement or even loss.

In FIG. 11, the front finger 106 is deleted to allow a better view of the head 40. For reloading, the head 40 is aligned with the pin 166, which is introduced to rest in the alignment bore 116. The pin 166 is long enough to prevent the fingers 106 of the grip 8 to be damaged by the base 162. While the housing 202 is held vertically, the rod 172 is entered into the loading opening 150 until seated on the jacket back 35. It is noted that the large diameter of the loading opening 150 permits a rod 172 of large diameter. This ensures a footprint large enough to ensure but light surface pressure on the jacket back 35, to prevent breakage.

To reload the RUTI 200, the handle 174 is firmly gripped, and forcefully lowered against and in the direction of the supporting surface 164, for the pin 166 and the rod 172 to put pressure on, respectively, the bolt 6 and the jacket 34, thereby compressing the spring 4. When the spring 4 is fully compressed, the piston 38 resides inside the jacket 34 with the teeth 86 seated inside the groove 94. While still retaining the spring 4 fully compressed, the catch, indicated by the numeral 14 in FIG. 1, is operated by lifting the housing 202 backwards, relative to the jacket 34, for the inner annular surface 60 of the housing to cover the support surface 90 of the jacket. The bolt 6, the jacket 34 and the housing 202 are now mutually locked in place. The spring 4 thus resides in the compressed condition and the RUTI 200 is reloaded, but not yet operative. The back tool 170 is now removed.

In turn, the safety 28 is inserted through the passages 33 to protrude transversally from the housing 202 and the RUTI 200 is removed from the front tool 162. For repeated use, the needle 10, previously used or brand new, is inserted into the grip 8 and the casing 20, already attached to the gage 22, is coupled to the external screw-thread 72 of the jacket 34. The RUTI 200 is now fully reloaded, assembled, and ready for repeated use. The compressed condition of the spring 4, seen through the transparent walls of the housing 2 and of the jacket 34, and the safety 28, clearly indicate that the RUTI 200 is ready for use. Evidently the safety 28, extending out of the housing 220 is the ultimate proof.

Figures 12A, 12B, 12C:
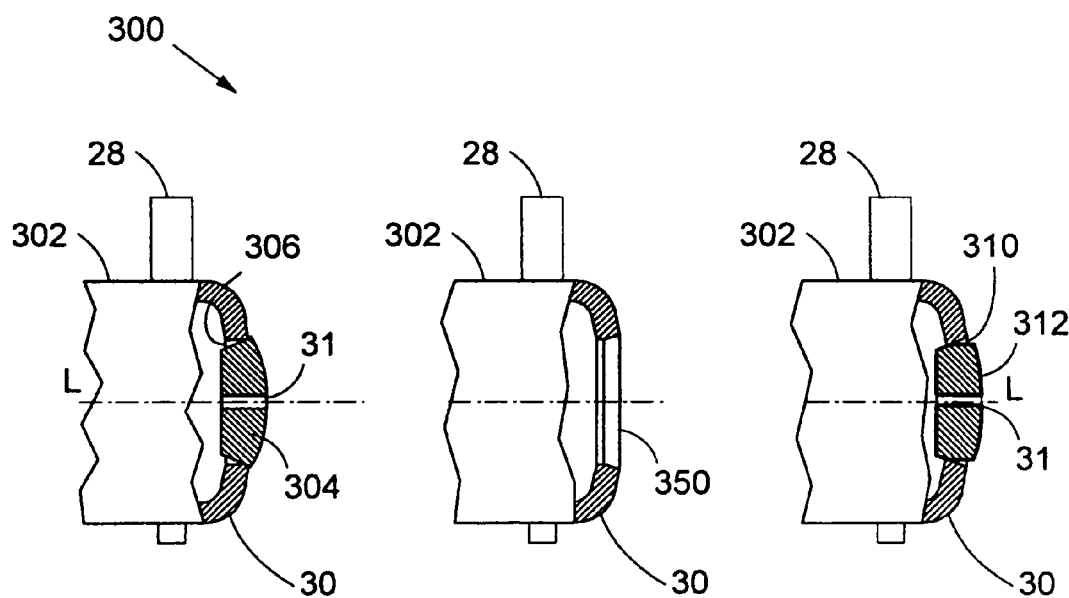

FIGS. 12a, 12b and 12c depict details of a further embodiment 300, or a RUTI 300, reconfigurable in situ. With the RUTI 300, the housing is designated as housing 302 in correspondence with the housing 2 of the SSTI. The bottom 30 of the housings 2 and of the housing 302 have the same general shape but the RUTI 300 allows to discern between the very first use and a repeated use.

With reference to FIG. 12a, the RUTI 300 is shown prior to the first use, with the bottom 30 closed by a cap 304 with a perforation 31, permitting the insertion therein of an opening tool such as a pull-out pin, to break away the cap 304 and form an open loading opening 350, when necessary or when so desired. The bottom 30 of the housing 302 is configured for severance and retrieval therefrom of the cap 304 shaped as a dome, so as to create a circular openable closed loading opening 350, shown open in FIG. 12b. A circular inside weakening relief 306 is manufactured on the bottom 30, on the inside of the housing 302, so that when a cap removal tool such as the pull-out pin 308 is inserted into the housing perforation 31, the cap 304 may be broken away from the bottom 30 and removed. The pull-out pin 308 seen in FIG. 11, is attached to the handle 174 as a cylindrical pin, longer than the thickness of the cap 304 and with a diameter allowing free passage via the housing perforation 31. If desired, the cap removal tool is configured differently, for example with a hook. Furthermore, the openable closed loading opening 350 is not necessarily circular, but must permit passage of the rod 172, which may received a cross-section other than round.

In FIG. 12c, as an alternative, an outside weakening relief 310 may be manufactured on the bottom 30, on the outside of the housing 302. Furthermore, the cap 304 may be thickened, to form a thick cap 312. Such a thickened cap may allow the pull-out pin 308 to ensure a cleaner breakaway of the thick cap 304 from the housing 302, and a better tactile signal to the user.

In principle, reloading of a RUTI 200 or 300, for repeated use requires the application of an axial force to recompress the spring 4. Such an axial force is applied either as described above, or by the intermediary of mechanisms using a screw thread, a ratchet, or a piston, to be integrated in tools configured as either portable or static tools.

In a further embodiment 1100, not illustrated, such as a C-clamp, also called G-clamp, chosen with sufficient clamping span, the clamping extremity of the adjusting screw is terminated with a rod sized as the rod 172, while the static jaw is equipped with a pin 166, in alignment with the longitudinal axis of the adjusting screw. This simple loading tool does not need to be explained.

Figure 13:
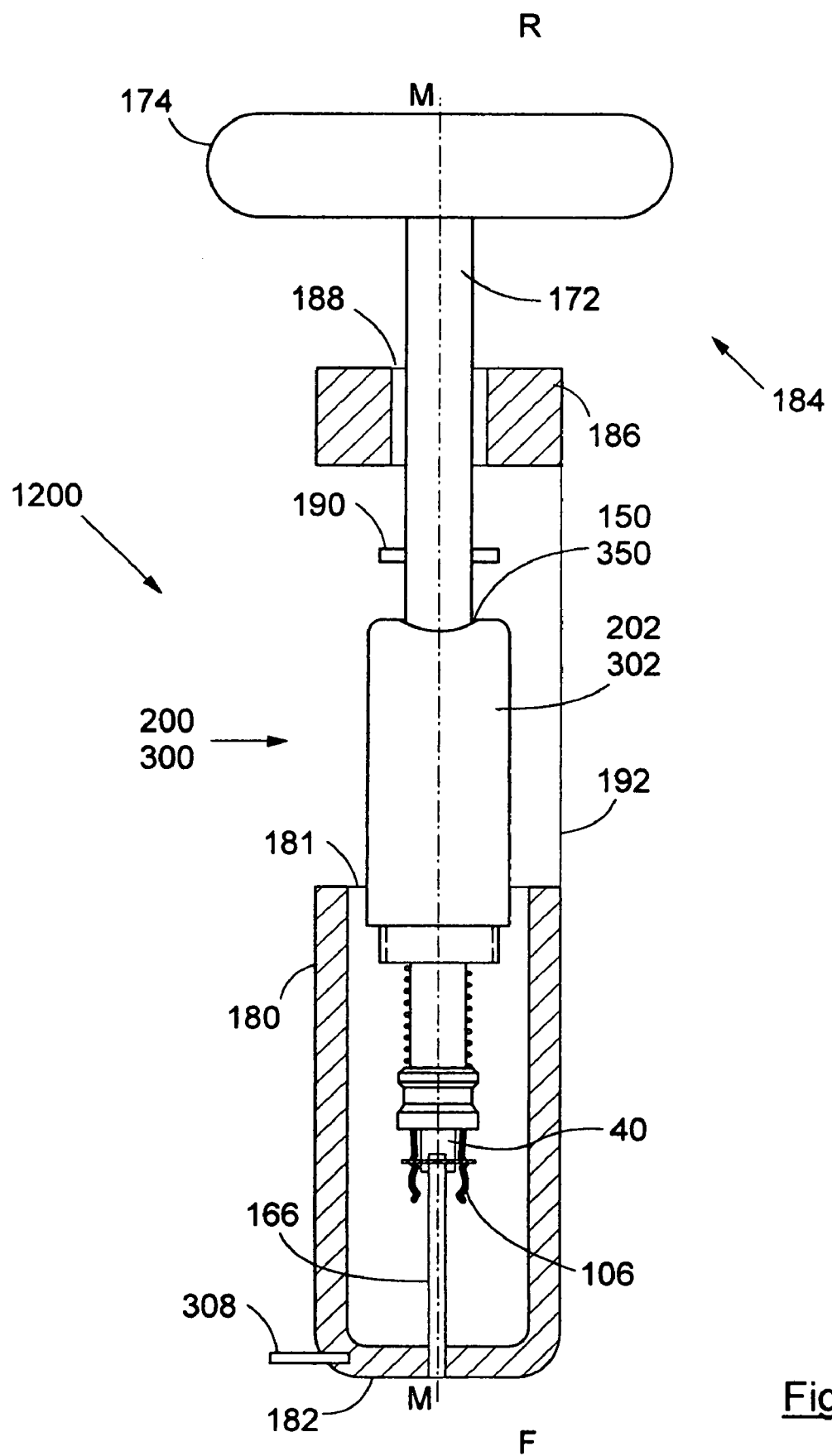
FIG. 13 illustrates a second embodiment of a loading tool engaged with the RUTI seen in FIG. 10.

With reference to FIG. 13, an integrated tool 1200 is schematically shown as a simple push-tool embodiment, having a longitudinal axis M—M. A cylindrically shaped coaxial front receptacle 180, with a rear opening 181 and a closed front end 182, both perpendicular to the axis M—M, is accommodated to receive a spent RUTI 200 or 300. The spent RUTI, either 200 or 300, is introduced into the front receptacle 180 with the axis L—L in alignment with the axis M—M. The closed front end 182 fixedly retains a pin 166 configured to coaxially support the head 40 by penetrating into the alignment bore 116. Furthermore, an opening tool such as a pull-out pin 308 may be rigidly affixed to the front receptacle 180 or to any other part of the integrated tool 1100 convenient for that purpose. In FIG. 13 the front-finger 106 is cut off to expose the head 40. The front portion of the housing, 202 or 302, is kept circumferentially captive in the front receptacle 180, which may surround the housing 202 or 302, completely for 360°, or for only more than a 180°, or even for less than 180°.

A rear portion 184 of the loading tool 1200 comprises a rod 172 inserted into the housing 202 or 302, via the loading opening or openable loading opening, respectively 150 or 350, in alignment with the pin 166. The rod 172 is coupled in perpendicular to a handle 174.

A rear guide 186, perpendicular to the longitudinal axis M—M, comprises a guide bore 188 coaxial with the pin 166 to slidingly receive the rod 172. To prevent exit of the rod 174 from the guide bore 188, a retaining member 190, for example a pin, is transversally inserted into the rod 172 frontward of the rear guide 186. The rear guide 186 is coupled to the front receptacle 180 by a connection rib 192. Operation of the handle 174 provides a longitudinal motion in alignment with the housing 202 or 302, and with the pin 166. To ease reloading, a handle bar 194, not shown in FIG. 13, may be attached to the front receptacle 180, or to the connection rib 192. Operation of the integrated tool 1100 is straightforward, generally as explained above, and does not require further details.

In an additional embodiment 1300 of a loading tool, similar to a caulking-gun, the moving end plate is replaced by a rod 172 as a termination for the serrated bar and the front receptacle is configured to hold a protruding pin 166. Again, this so simple concept does not require a drawing or a description, neither of structure, nor of operation.

In general, any appropriately configured powered piston type device, mechanic, pneumatic, hydraulic or electric, may be used to assist with the recompression of the spring 4.

While preferred embodiments have been shown and described in detail, it should be apparent that many modifications and variations thereto are possible, all of which fall within the true spirit scope of the invention. For example, the bottom 30 of the housing 202 and 302 may be configured in different shapes and the loading tool may comprise an automatic mechanism for locking the housing 202 and 302 relatively to the jacket 34, by sliding the inner annular surface 60 over the support surface 90.

The various loading tools, related to as embodiments 1000, 1100, 1200 and 1300 are evidently configured to operate with the different RUTIs, in the embodiments 200 and 300. Moreover, the various loading tools are easily configured for reloading of a RUTI embodiment comprising more than one loading opening. The shape of the loading opening may be selected at will and differ from the circular shape described above. Furthermore, for a RUTI embodiment with more than one loading opening, each opening may exhibit a different shape.

Whilst the foregoing description described the insertion of a trocar-needle into a bone, the procedure is not restricted to humans, but is applicable to animals. Furthermore, the insertion technique is also pertinent for plants, such as trees, and for foodstuff, such as cheese.

It will be appreciated by persons skilled in the art, that the present invention is not limited to what has been particularly shown and described hereinabove. Rather, the scope of the present invention is defined by the appended claims and includes both combinations and subcombinations of the various features described hereinabove as well as variations and modifications thereof which would occur to persons skilled in the art upon reading the foregoing description.

The invention claimed is:

1. A repeated use trocar-needle insertion gun (RUTI) operating in association with a loading tool, comprising:
    a needle portion of the RUTI being configured for gripping a trocar-needle before insertion into a bone, and for release of the trocar-needle upon insertion into the bone,
    a front portion of the RUTI being configured for adjusting insertion-depth of the trocar-needle into the bone, and for protecting the trocar-needle prior to release,
    a rear portion of the RUTI having a shooting mechanism operative for shooting the trocar-needle, and a catch adapted for retaining the shooting mechanism, and for releasing the shooting mechanism when triggered for shooting, and the front portion being releasably coupled to the rear portion, the rear portion comprising:
    a housing having a housing inside, a housing outside and a housing bottom,
    at least one spring disposed inside the housing and residing in a first compressed condition associated with a loaded state of the RUTI before shooting the trocar-needle, and in a second released condition associated with a spent state of the RUTI after shooting the trocar-needle,
    at least one open loading opening being accommodated in the bottom of the housing of the RUTI to provide access therethrough, from the outside to the inside, for coupling the loading tool with the at least one spring, and
    a loading tool configured for coupling with and operative for reloading the RUTI in situ from the spent state to the loaded state via the at least one loading opening.

2. The RUTI and the loading tool, according to claim 1, wherein:

the at least one loading opening obviates the need for disassembly of the rear portion of the RUTI when using the loading tool to reload the RUTI from the spent state to the loaded state.

3. The RUTI and the loading tool, according to claim 1, wherein:

the at least one loading opening in the RUTI has one single bore, and the loading tool is operable to reload the RUTI via the one single bore.

4. The RUTI and the loading tool, according to claim 1, wherein:

the at least one loading opening has either one out of two configurations comprising:

a readymade open loading opening, and an openable closed loading opening accommodated for intentional opening in situ.

5. The RUTI and the loading tool, according to claim 4, wherein:

the open openable closed loading opening is indicative of prior use of the RUTI.

6. The RUTI and the loading tool, accordinq to claim 1, wherein:

the at least one open loading opening indicates that the RUTI is configured for more than one single use.

7. The RUTI and the loading tool according to claim 1, wherein:

when reloaded from the spent state to the loaded state the RUTI becomes operative for at least one repeated trocar-needle insertion use after grippingly mounting a trocar-needle and after coupling the front portion to the rear portion.

8. The RUTI and the loading tool according to claim 1, wherein:

when reloaded with the loading tool, the RUTI is operative with either one of both a previously used trocar-needle and a new unused trocar-needle.

9. The RUTI and the loading tool, according to claim 1, wherein:

the at least one spring in the RUTI has a proximal end disposed closer to the front portion in alignment with a distal end distanced away from the front portion, and the loading tool has at least one compression force application element configured for passage from the outside to the inside of the housing of the RUTI via the at least one loading opening, and is configured for application of compressive force to, and in alignment with the proximal end and the distal end of the at least one spring, for return of the at least one spring from a released condition to a compressed condition when the loading tool is coupled to and operated on the RUTI, whereby the RUTI is returned from the spent state to the loaded state.

10. The RUTI and the loading tool according to claim 1, wherein:

the catch is operable for releasably retaining the at least one spring in compressed condition, and when the RUTI is reloaded and the at least one spring is returned to compressed condition, the catch is operable for releasing the shooting mechanism.

11. The RUTI and the loading tool according to claim 1, wherein:

the at least one spring has a proximal end disposed closer to the front portion, and a distal end distanced away from the front portion, and the loading tool has a front tool portion configured for operation in association with the proximal end of the at least one spring, and a back tool portion having an element configured for penetration from the outside to the inside of the RUTI via the at least one loading opening in association with the distal end of the at least one spring, the loading tool being configured for application of compressive force to the front tool portion and to the back tool portion, to return the at least one spring from released condition to compressed condition.

12. The RUTI and the loading tool according to claim 11, wherein:

the loading tool has a distal portion and a proximal portion disposed in mutual alignment, and also aligned with, respectively, the distal end and the proximal end of the at least one spring of the RUTI when coupled thereto, the proximal portion being coupled with the proximal end and the distal portion penetrating via the at least one loading opening for coupling with the distal end, wherein when operated, the loading tool forces translation of at least either one of both the distal portion and the proximal portion to compress the at least one spring.

13. The RUTI and the loading tool according to claim 11, wherein:

the loading tool has at least one actuator configured for reloading the RUTI and allowing operation of the catch when compressed condition of the at least one spring is reached, and the at least one actuator is selected, alone and in combination, from the group consisting of manual, pneumatic, hydraulic, electric and magnetic actuators.

14. The RUTI and the loading tool according to the claims 1, wherein:

the at least one spring has a proximal end disposed closer to the front portion, and a distal end distanced away from the front portion, and the loading tool has:

a distal support and a proximal support adapted for coupling with respectively, the distal end and the proximal end of the at least one spring, and a loading mechanism configured for application of mutually compressive forces and for providing relative motion to at least one of the distal and of the proximal support, for return of the at least one spring from released condition to compressed condition, and permitting operation of the catch to releasably retain the at least one spring in compressed condition.

\* \* \* \* \*